US010638950B2

(12) United States Patent
Fujikawa et al.

(10) Patent No.: US 10,638,950 B2
(45) Date of Patent: May 5, 2020

(54) MAGNETIC RESONANCE IMAGING APPARATUS, STATIC MAGNETIC FIELD HOMOGENEITY ADJUSTMENT METHOD, PROGRAM, AND COMPUTER

(71) Applicant: HITACHI, LTD., Tokyo (JP)

(72) Inventors: Takuya Fujikawa, Tokyo (JP); Mitsushi Abe, Tokyo (JP); Kenji Sakakibara, Tokyo (JP); Hikaru Hanada, Tokyo (JP)

(73) Assignee: HITACHI, LTD., Tokyo (JP)

(*) Notice: Subject to any disclaimer, the term of this patent is extended or adjusted under 35 U.S.C. 154(b) by 375 days.

(21) Appl. No.: 15/543,381

(22) PCT Filed: Feb. 10, 2016

(86) PCT No.: PCT/JP2016/053882
§ 371 (c)(1),
(2) Date: Jul. 13, 2017

(87) PCT Pub. No.: WO2016/136465
PCT Pub. Date: Jan. 9, 2016

(65) Prior Publication Data
US 2017/0354343 A1 Dec. 14, 2017

(30) Foreign Application Priority Data
Feb. 25, 2015 (JP) .................. 2015-034786

(51) Int. Cl.
G01R 33/38 (2006.01)
A61B 5/055 (2006.01)
(Continued)

(52) U.S. Cl.
CPC .......... A61B 5/055 (2013.01); G01R 33/3873 (2013.01); G01R 33/385 (2013.01); G01R 33/3815 (2013.01)

(58) Field of Classification Search
CPC ... A61B 5/055; G01R 33/3873; G01R 33/385
See application file for complete search history.

(56) References Cited

U.S. PATENT DOCUMENTS 6,291,998 B1 * 9/2001 Heid ................. G01R 33/3875
324/313
6,600,318 B1 * 7/2003 Kakugawa ......... G01R 33/3806
324/318

(Continued)

FOREIGN PATENT DOCUMENTS

JP 11-318859 11/1999
JP 2011-115480 6/2011
(Continued)

OTHER PUBLICATIONS

International Search Report dated May 10, 2016 in connection with PCT/JP2016/053882.
(Continued)

Primary Examiner — Giovanni Astacio-Oquendo
Assistant Examiner — Alvaro E Fortich
(74) Attorney, Agent, or Firm — Cooper & Dunham LLP

(57) ABSTRACT

In order to provide a static magnetic field homogeneity adjustment method capable of reducing an arrangement amount of magnetic pieces and achieving desired magnetic field homogeneity with high accuracy in magnetic field homogeneity adjustment, there is provided a static magnetic field homogeneity adjustment method in an imaging space of computing positions of a plurality of magnetic pieces separated from the imaging space through shimming computation with respect to a static magnetic field in the imaging space generated by a magnetic field generation device, and disposing the plurality of magnetic pieces at the positions obtained through the shimming computation, the method including an adjustment step of imposing restriction that a polarity of a magnetic field distribution generated in the
(Continued)

imaging space by the magnetic pieces disposed at the positions is either positive or negative during the shimming computation, and adjusting the static magnetic field homogeneity.

6 Claims, 17 Drawing Sheets

(51) Int. Cl.
    *G01R 33/3873*    (2006.01)
    *G01R 33/3815*    (2006.01)
    *G01R 33/385*    (2006.01)

(56) References Cited

U.S. PATENT DOCUMENTS

| | | | |
|---|---|---|---|
| 7,315,168 B2* | 1/2008 | Rapoport | G01R 33/3875 324/320 |
| 2011/0089943 A1 | 4/2011 | Abe et al. | |
| 2012/0176136 A1* | 7/2012 | Shinagawa | G01R 33/3815 324/322 |
| 2012/0268119 A1* | 10/2012 | Abe | G01R 33/3873 324/307 |
| 2013/0038328 A1 | 2/2013 | Iwasa et al. | |
| 2014/0009152 A1 | 1/2014 | Sakikabara | |
| 2014/0329689 A1* | 11/2014 | Tanabe | A61B 5/055 505/211 |
| 2015/0102809 A1* | 4/2015 | van Beek | G01R 33/443 324/309 |

FOREIGN PATENT DOCUMENTS

| | | |
|---|---|---|
| JP | 2012-249765 | 12/2012 |
| WO | WO2009/136643 A1 | 11/2009 |
| WO | WO2012/132911 A1 | 10/2012 |

OTHER PUBLICATIONS

Chinese official action (and machine translation thereof into English) dated Nov. 4, 2019 in corresponding Chinese Patent Application No. 201680004608.9.

* cited by examiner

FIG.6

ROUGH ADJUSTMENT SHIMMING

SHIM IRON USE AMOUNT : 672[cc]

| SHIM IRON | W×H mm | T mm |
|---|---|---|
| A | 20×20 | 0.1 |
| B | 20×20 | 0.02 |

FIG.7

FINE ADJUSTMENT SHIMMING

SHIM IRON USE AMOUNT : 28[cc]

| SHIM IRON | W×H mm | T mm |
|---|---|---|
| A | 20×20 | 0.1 |
| B | 20×20 | 0.02 |

SHIM POCKET NUMBER

| Tray \ Pocket | p-6 | p-7 | p-8 | p-9 | p-10 | p-11 | p-12 | p-13 | p-14 | p-15 | p-16 | p-17 | p-18 | p-19 |
|---|---|---|---|---|---|---|---|---|---|---|---|---|---|---|
| #2 | | | | A:9 B:4 | A:1 B:0 | | A:2 B:0 | | A:2 B:0 | A:0 B:5 | | A:1 B:0 | A:1 B:0 | |
| #4 | A:0 B:1 | A:2 B:4 | A:0 B:3 | | A:2 B:2 | A:0 B:2 | A:1 B:3 | | A:3 B:1 | | | A:9 B:4 | A:2 B:2 | A:5 B:2 |
| #6 | | A:2 B:2 | A:2 B:2 | A: B: | A:0 B:4 | | A:0 B:4 | | A:1 B:2 | A:1 B:3 | A:1 B:2 | A:2 B:2 | A:2 B:2 | |
| #8 | A:1 B:0 | | A:1 B:0 | A:3 B:1 | A:3 B:1 | | | A:1 B:0 | A:1 B:2 | A:1 B:0 | | | A:2 B:2 | A:0 B:4 |
| #10 | A:2 B:2 | A:2 B:2 | | | | A:2 B:2 | | A:1 B:0 | | A:1 B:3 | A:1 B:1 | | A:1 B:2 | A:5 B:2 |
| #12 | A:1 B:0 | A:2 B:2 | A:1 B:3 | | A:1 B:0 | A:0 B:4 | A:0 B:4 | | | A:1 B:3 | | | A:1 B:0 | |
| #14 | | A:2 B:4 | A:2 B:2 | | A:1 B:0 | A:2 B:2 | A:2 B:4 | | A:5 B:1 | | A:1 B:1 | A:2 B:2 | A:2 B:4 | |
| #16 | | | A:1 B:3 | A:2 B:2 | | A:2 B:4 | A:2 B:4 | A:2 B:2 | A:2 B:2 | A:2 B:2 | A:4 B:4 | A:2 B:2 | A:2 B:4 | |
| #18 | | A:2 B:4 | A:2 B:2 | | | A:3 B:1 | A:2 B:2 | | A:2 B:2 | | | | | |
| #20 | A:2 B:0 | | A:1 B:3 | | | A:1 B:0 | A:2 B:2 | | | A:2 B:2 | A:2 B:4 | A:2 B:4 | A:1 B:0 | A:1 B:2 |
| #22 | A:2 B:0 | A:2 B:4 | A:2 B:2 | A:2 B:2 | | A:2 B:2 | A:2 B:2 | A:2 B:2 | | A:2 B:4 | A:2 B:2 | A:2 B:0 | | |
| #24 | A:1 B:0 | | A:1 B:2 | | | A:2 B:2 | | | A:1 B:3 | | A:2 B:2 | A:2 B:0 | | A:1 B:2 |

SHIM TRAY NUMBER

FIG.13

ROUGH ADJUSTMENT SHIMMING

SHIM IRON USE AMOUNT : 220[cc]

| SHIM TRAY NUMBER \ SHIM POCKET NUMBER | A | B | C | D | E | F | G | H | I | J | K | L |
|---|---|---|---|---|---|---|---|---|---|---|---|---|
| #1 | | | | 0 | 0 | 1 | 1 | 1 | 0 | | | |
| #2 | | | 1 | 0 | 0 | 2 | 2 | 2 | 11 | 0 | | |
| #3 | | 4 | 2 | 0 | 0 | 0 | 1 | 2 | 2 | 0 | 0 | |
| #4 | 0 | 5 | 3 | 0 | 2 | 1 | 0 | 1 | 2 | 1 | 1 | 0 |
| #5 | 2 | 2 | 0 | 1 | 1 | 1 | 0 | 2 | 0 | 2 | 1 | 2 |
| #6 | 3 | 4 | 6 | 0 | 0 | 5 | 2 | 4 | 0 | 2 | 2 | 1 |
| #7 | 5 | 6 | 3 | 4 | 0 | 0 | 1 | 0 | 2 | 0 | 2 | 1 |
| #8 | 4 | 0 | 4 | 3 | 2 | 3 | 6 | 5 | 5 | 0 | 1 | 0 |
| #9 | 0 | 0 | 3 | 4 | 3 | 4 | 1 | 3 | 4 | 2 | 1 | 0 |
| #10 | | 1 | 1 | 2 | 2 | 0 | 6 | 1 | 2 | 4 | 0 | |
| #11 | | | 3 | 1 | 3 | 2 | 0 | 3 | 0 | 3 | | |
| #12 | | | | 0 | 4 | 4 | 1 | 2 | 1 | | | |

FINE ADJUSTMENT SHIMMING

SHIM IRON USE AMOUNT : 140[cc]

| SHIM TRAY NUMBER \ SHIM POCKET NUMBER | A | B | C | D | E | F | G | H | I | J | K | L |
|---|---|---|---|---|---|---|---|---|---|---|---|---|
| #1 | | | | | | | | | | | | |
| #2 | | | | | | | | | | | | |
| #3 | | | | | 1 | 2 | 2 | 1 | | | | |
| #4 | | | | 0 | 2 | 4 | 0 | 0 | 1 | | | |
| #5 | | | 1 | 3 | 5 | 2 | 1 | 0 | 2 | 0 | | |
| #6 | | | 0 | 0 | 0 | 2 | 5 | 2 | 4 | 0 | | |
| #7 | | | 2 | 0 | 2 | 6 | 2 | 1 | 1 | 0 | | |
| #8 | | | 0 | 4 | 3 | 0 | 0 | 2 | 1 | 2 | | |
| #9 | | | | 1 | 2 | 2 | 1 | 2 | 0 | | | |
| #10 | | | | | 0 | 1 | 1 | 0 | | | | |
| #11 | | | | | | | | | | | | |
| #12 | | | | | | | | | | | | |

10

MAGNETIC RESONANCE IMAGING APPARATUS, STATIC MAGNETIC FIELD HOMOGENEITY ADJUSTMENT METHOD, PROGRAM, AND COMPUTER

TECHNICAL FIELD

The present invention relates to a magnetic resonance imaging apparatus, a static magnetic field homogeneity adjustment method, a program, and a computer.

BACKGROUND ART

High magnetic field homogeneity (for example, a difference between the maximum value and the minimum value of a magnetic field is several ppm or less) in an imaging space (field of view: FOV) near the magnetic field center is required for a magnetic field generation device mounted on a magnetic resonance imaging (MRI) apparatus. However, actually, the high magnetic field homogeneity is disturbed due to the influence of a manufacturing dimension error in a manufacturing stage of the MRI apparatus or the influence of magnetic bodies around a location where the MRI apparatus is provided.

Therefore, in the MRI apparatus, the homogeneity of magnetic field intensity in an FOV is finely adjusted (hereinafter, referred to as shimming). As an example of shimming, there is passive shimming in which shim pieces of correction magnetic bodies (hereinafter, referred to as magnetic pieces) are disposed around an FOV, and a static magnetic field distribution is finely adjusted. The passive shimming is a method of adjusting a static magnetic field distribution of an FOV to desired homogeneity by disposing an appropriate amount of magnetic pieces at an appropriate position through optimization computation (refer to PTLs 1 and 2). In other words, the homogeneity of the static magnetic field distribution of the FOV is adjusted by a magnetic field distribution generated by magnetic moment of the magnetic pieces disposed in a magnetic field.

CITATION LIST

Patent Literature

PTL 1: JP-A-2014-4169
PTL 2: JP-A-2011-115480

SUMMARY OF INVENTION

Technical Problem

However, PTLs 1 and 2 do not disclose that a magnetic field distribution of magnetic moment generated in an FOV, especially, a polarity is changed depending on a position where magnetic pieces are disposed. As a result, in shimming performed a plurality of number or times, there is a problem in that an amount of disposed magnetic pieces may be rather increased in fine adjustment shimming performed in a case where a total iron amount of magnetic pieces is smaller than a total iron amount of magnetic pieces used in the first shimming (for example, 1/10 or less).

For example, in a cylindrical electromagnet, magnetic pieces disposed near a bore opening separated from an FOV generate a positive direction magnetic field with respect to a static magnetic field of the FOV, but has low performance of adjusting the static magnetic field since a distance thereof from the FOV is long. On the other hand, magnetic pieces in a region close to the FOV generate a negative direction magnetic field with respect to the static magnetic field of the FOV, but has high performance of adjusting the static magnetic field since a distance thereof to the FOV is short. Therefore, if a plurality of magnetic pieces are disposed from the vicinity of the bore opening separated from the FOV to the region close to the FOV, static magnetic field adjustment performances of the magnetic pieces are canceled out, and thus an arrangement amount of magnetic pieces may be increased.

As mentioned above, if an arrangement amount of magnetic pieces is increased, there is a case where discrete errors increase, the accuracy of shimming is reduced, and thus desired magnetic field homogeneity cannot foe achieved. If an arrangement amount of magnetic pieces is increased, there is a case where an error easily occurs in an arrangement position, and the workability of fine adjustment shimming is reduced.

An object of the invention is to provide a static magnetic field homogeneity adjustment method for a magnetic resonance imaging apparatus, capable of reducing an arrangement amount of magnetic pieces and thus achieving desired magnetic field homogeneity with high accuracy in magnetic field homogeneity adjustment.

Solution to Problem

In order to achieve the object, according to the invention, there is provided a static magnetic field homogeneity adjustment method in an imaging space of computing positions of a plurality of magnetic pieces separated from the imaging space through shimming computation with respect to a static magnetic field in the imaging space generated by a magnetic field generation device, and disposing the plurality of magnetic pieces at the positions obtained through the shimming computation, the method including an adjustment step of imposing restriction that a polarity of a magnetic field distribution generated in the imaging space by the magnetic pieces disposed at the positions is either positive or negative during the shimming computation, and adjusting the static magnetic field homogeneity.

According to the invention, it is possible to reduce a total arrangement amount of magnetic pieces and achieve desired magnetic field homogeneity with high accuracy in magnetic field homogeneity adjustment. For example, a total use amount of the magnetic pieces can be reduced to about 65% compared with the related art. An effect can be expected in which the influence of a discrete error can be reduced, or work time can be reduced in a fine adjustment process in shimming, due to the reduction in a total amount of magnetic pieces.

Advantageous Effects of Invention

According to the invention, it is possible to provide a static magnetic field homogeneity adjustment method for a magnetic resonance imaging apparatus, capable of reducing an arrangement amount of magnetic pieces and thus achieving desired magnetic field homogeneity with high accuracy in magnetic field homogeneity adjustment.

BRIEF DESCRIPTION OF DRAWINGS

FIG. 6 is a diagram illustrating arrangement of magnetic pieces in rough adjustment shimming according to the first embodiment.

FIG. 7 is a diagram illustrating arrangement of magnetic pieces in fine adjustment shimming according to the first embodiment.

FIG. 13 is a diagram illustrating arrangement of magnetic pieces in rough adjustment shimming according to the second embodiment.

FIG. 14 is a diagram illustrating arrangement of magnetic pieces in fine adjustment shimming according to the second embodiment.

DESCRIPTION OF EMBODIMENTS

Hereinafter, a magnetic resonance imaging apparatus and a static magnetic field homogeneity adjustment method of the invention will be described on the basis of embodiments.

First Embodiment

Figure 1:
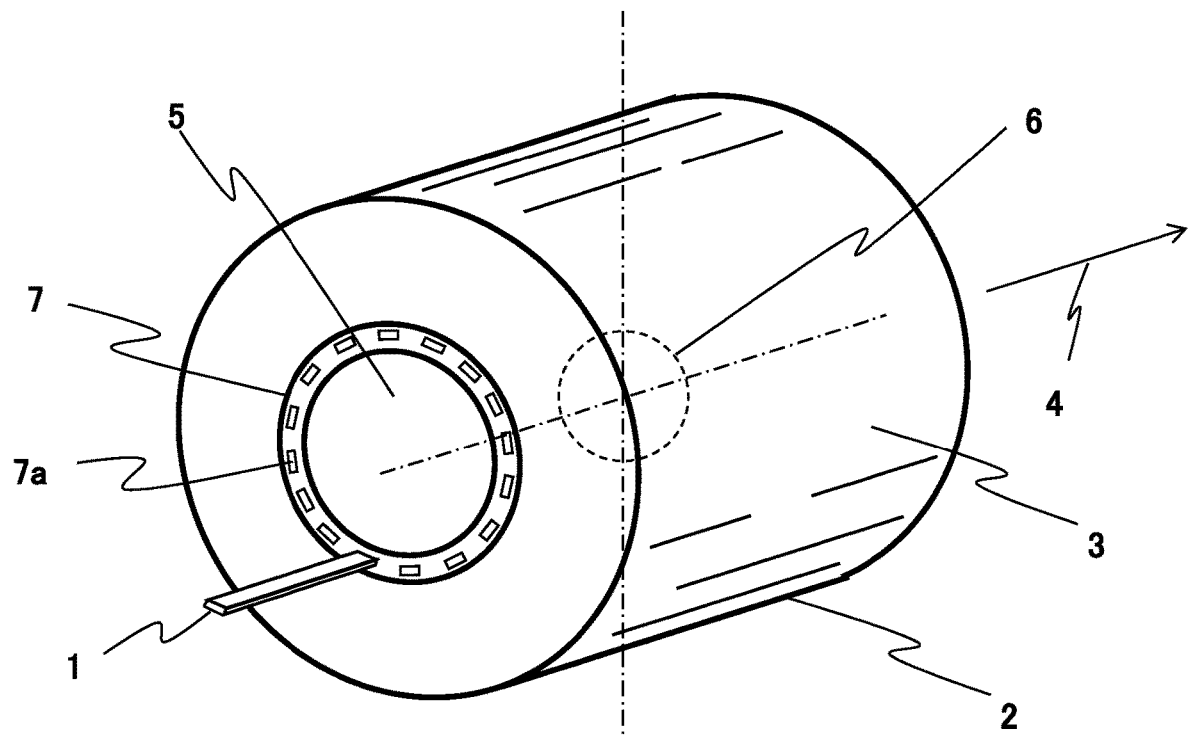
FIG. 1 is a schematic configuration diagram of a cylindrical superconducting magnet including a shimming mechanism of a magnetic resonance imaging apparatus according to a first embodiment of the invention.

FIG. 1 is a schematic exterior perspective view of a cylindrical superconducting magnet 2 of a magnetic resonance imaging apparatus according to a first embodiment. The superconducting magnet 2 can generate a high magnetic field, but the invention may be applied to a normal conducting electromagnet.

In the figure, the superconducting magnet 2 is formed by accommodating a refrigerant inside a vacuum container 3 along with a superconducting coil (not illustrated) which is a main coil. The superconducting magnet 2 includes an imaging space (FOV) 6 which images an object in an internal space of a cylindrical bore 5 which has an axial direction (Z axis) 4 which is parallel to a horizontal direction as a central axis. The superconducting magnet 2 generates a static magnetic field which is substantially spherical, homogeneous in magnetic field intensity, and also constant in a magnetic field direction, in the FOV 6.

Figure 2:
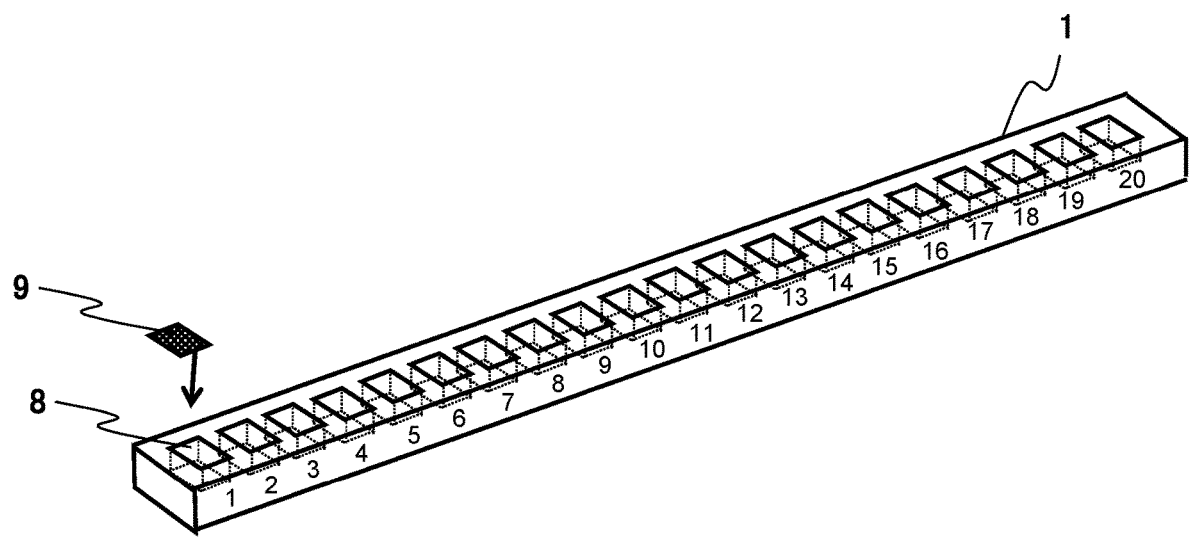
FIG. 2 is a configuration diagram of a shim tray of the cylindrical superconducting magnet according to the first embodiment.

A gradient magnetic field coil 7 is accommodated on an inner surface of the cylindrical bore 5 on the FOV 6 side, a plurality of holes 7a are provided inside the gradient magnetic field coil 7 at intervals of an equal angle in a circumferential direction, a shim tray 1 is attachably and detachably inserted into each of the holes 7a. The shim tray 1 is used for passive shimming, any number # is assigned to each shim tray 1, and shimming can be performed by individually selecting each shim tray on the basis of the number. As illustrated in FIG. 2, the shim tray 1 has a length corresponding to an axial direction length of the cylindrical bore 5, and is provided with a plurality of shim pockets 8 at predetermined positions in the length direction in a distribution manner. A plurality of magnetic pieces 9 can be stacked and disposed in each of the shim pockets 8.

The shim tray 1 storing the magnetic pieces 9 is made of a nonmagnetic material such as a resin. The shim tray storing the magnetic pieces 9 is fixed to a predetermined position in the superconducting magnet 2. Disturbance of a magnetic field in the FOV is adjusted by appropriately adjusting a thickness and an amount of magnetic pieces 9 stored in a predetermined location of the shim tray 1. In normal shimming, there is a case where the accuracy is low, and desired magnetic field homogeneity cannot be achieved due to the influence of a variation in magnetization of the magnetic pieces 9 disposed in the shim tray 1 or an error (hereinafter, referred to as a discrete error) of a shape of the magnetic piece 9 due to the minimum dimension or the like of the magnetic piece 9. In order to obtain desired magnetic field homogeneity, it is necessary to perform shimming a plurality of number of times.

Figure 5:
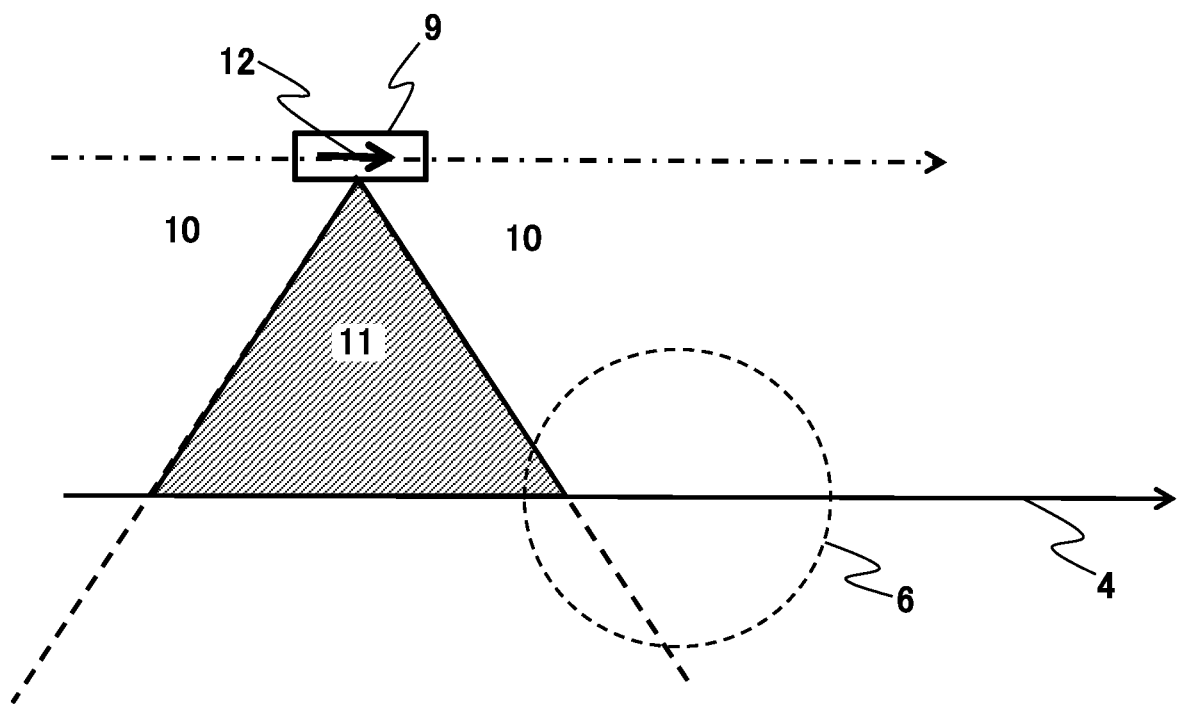
FIG. 5 is a diagram illustrating positive and negative magnetic field distributions generated in an FOV by magnetic moment of magnetic pieces according to the first embodiment.

Here, action of the passive shimming will be described. Generally, the magnetic piece 9 is made of a magnetic material with high permeability. As the magnetic material, a sheet magnetic body, for example, an iron sheet, preferably, a silicon steel sheet may be used. As illustrated in FIG. 5, a magnetic field which is generated by the magnetic piece 9 at a point separated by a position r in an orientation 12 of magnetization (an orientation of magnetic moment) of the magnetic piece is expressed as in the Equation 1, but a Bz component of an axial direction magnetic field treated in the passive shimming is expressed as in Equation 2.

$$B(r) = \frac{\alpha}{r^3} \left\{ \frac{3(\vec{M} \cdot \vec{r})\vec{r}}{r^2} - \vec{M} \right\} \quad (1)$$

B(r) is a magnetic field [T] generated at a point separated by the position r by magnetic moment.

M is magnetic moment [Am$^2$].

r is a position vector (r=(X,Y,Z)) of magnetic moment.

α is a coefficient.

$$Bz = \alpha \left\{ \frac{3Mx \cdot XZ}{r^5} + \frac{3My \cdot YZ}{r^5} + \frac{3Mz \cdot Z^2}{r^5} - \frac{Mz}{r^3} \right\} \quad (2)$$

Bz is a magnetic field [T] generated at a point separated by the position r by magnetic moment in the Z axis direction.

Mx is magnetic moment [Am²] in the X axis direction.
My is magnetic moment [Am²] in the Y axis direction.
Mz is magnetic moment [Am²] in the Z axis direction.

A magnetic field magnetizing the magnetic piece 9 is mainly directed in the Z axis direction, and thus Equation 3 is obtained focusing only on Mz. In other words, Bz expressed in the following Equation 3 is an amount which can be adjusted through shimming.

$$Bz = \alpha \left\{ \frac{3Mz \cdot Z^2}{r^5} - \frac{Mz}{r^3} \right\} \quad (3)$$

Z is a position in the Z axis direction.

Figure 4:
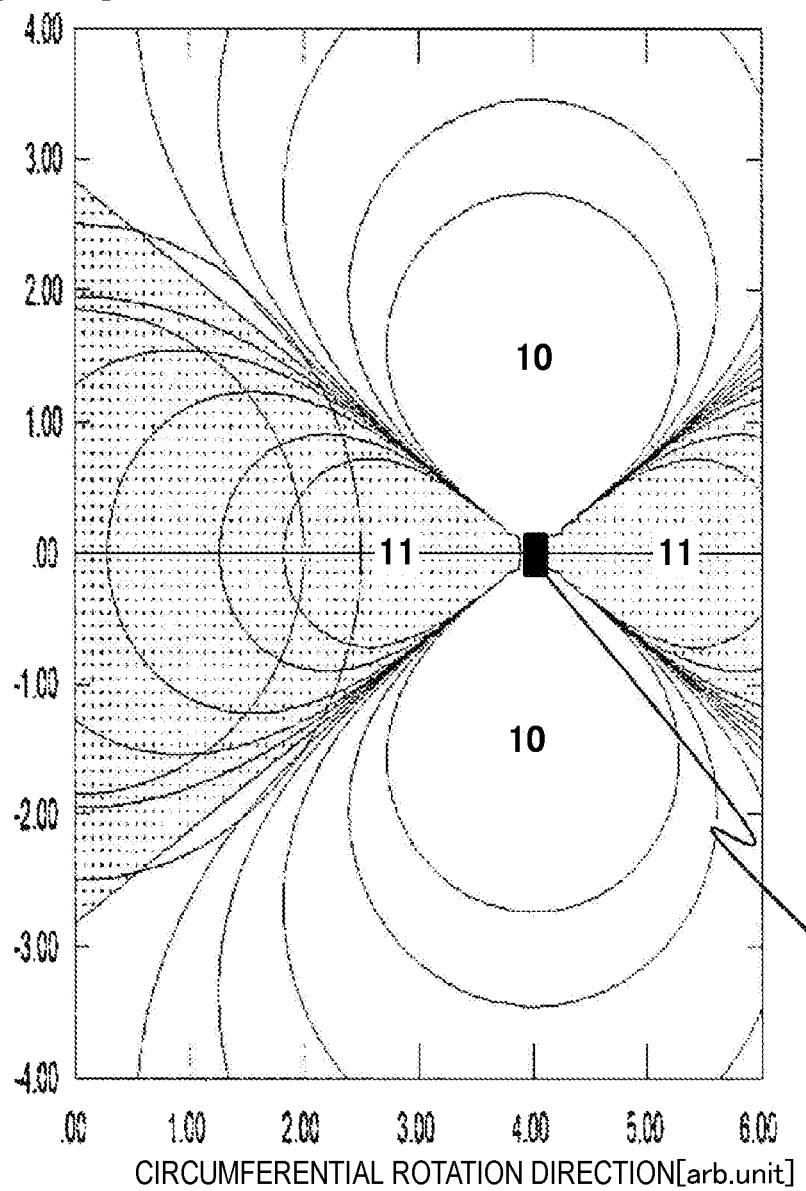
FIG. 4 is a diagram illustrating positive and negative magnetic field distributions generated by magnetic moment of magnetic pieces according to the first embodiment.

FIG. 4 is a diagram illustrating positive and negative magnetic field distributions generated in the FOV 6 by magnetic moment of the magnetic piece 9.

The Bz component generated by magnetic moment of the magnetic piece 9 is located in a positive region 10 and a negative region 11 with the following Equation 4 as a boundary.

$$\frac{3Mz \cdot Z^2}{r^5} - \frac{Mz}{r^3} = 0 \quad (4)$$

Z indicates a position in the Z axis direction.

FIG. 5 illustrates a relationship between a magnetization region of the Bz component generated by magnetic moment of the magnetic piece 9 used for shimming, the axial direction (Z axis) 4, and the FOV 6. An arrow of the magnetic moment indicates a direction of magnetization of the magnetic piece 9, and a two-dot chain line indicates an arrangement direction of the magnetic piece 9. In the present embodiment, out of positive and negative magnetic field distributions generated in the FOV 6 by the magnetic moment of the magnetic piece 9, the negative region 11 in which only the negative magnetic field distribution is generated is selected as a region in which magnetic pieces are disposed.

In fine adjustment shimming, positive and negative magnetic field distributions generated in the FOV by magnetic moment of the magnetic piece 9 is taken into consideration, and a region in which only a magnetic field distribution of either one of polarities is generated is selected as an arrangement region of the magnetic pieces 9 (in the present embodiment, a negative polarity is selected). For example, the arrangement region is restricted to a region in which the negative region of Bz overlaps the FOV region with Equation 4 as a boundary. Consequently, a total amount, of the magnetic pieces 9 to be disposed can be reduced, and desired magnetic field homogeneity can be achieved with high accuracy. An effect can be expected in which the influence of a discrete error can be reduced or work time can be reduced without an error of arrangement of the magnetic piece 9 in a fine adjustment process in shimming, due to the reduction in a total amount of magnetic pieces.

Figure 3:
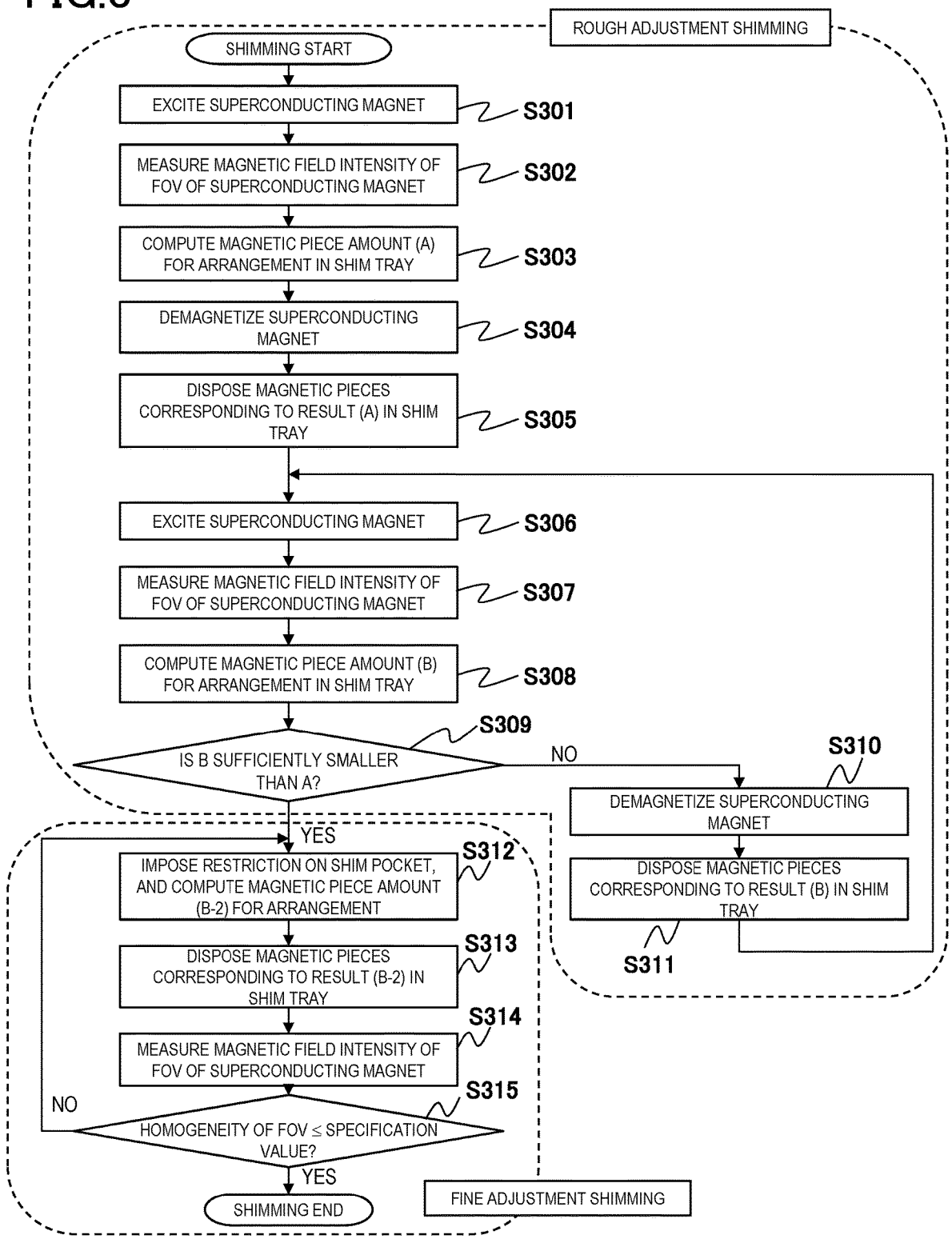
FIG. 3 is a flowchart illustrating shimming according to the first embodiment.

With reference to a flowchart illustrated in FIG. 3, a description will be made of procedures of shimming in the cylindrical superconducting magnet 2 according to the first embodiment. In the figure, step S301 to step S311 show rough adjustment shimming, and step S312 to step S315 show fine adjustment shimming. The shimming method of the invention has a feature in the fine adjustment shimming.

The fine adjustment shimming is performed in a case where a total amount of the magnetic pieces 9 used for shimming is sufficiently smaller than a total amount of the magnetic pieces 9 used for first shimming (for example, ¹⁄₁₀ or less). In other words, in the fine adjustment shimming, in order to obtain desired magnetic field homogeneity, the non-homogeneity (for example, the non-homogeneity of a magnetic field corresponding to a magnetic field component mainly of a low-order term in series expansion using a spherical harmonic function) of a low frequency component of a magnetic field distribution of the FOV 6 is adjusted.

First, in step S301, the superconducting magnet 2 is excited, and thus a static magnetic field is generated in the FOV 6. In step S302, a magnetic field measurement device (not illustrated) measures magnetic field intensity in the FOV 6.

In step S303, well-known optimization computation is performed by using the magnetic field intensity measured in step S302, and a magnetic piece amount (A) of the magnetic pieces 9 to be stored in shim pockets P (for example, P-1 to P-24) of some shim trays 1 (for example, odd-numbered shim trays 1) for canceling out the non-homogeneity of the magnetic field is determined. An arrangement diagram (for example, illustrated in FIG. 6) of the determined magnetic pieces 9 is output and displayed.

In step S304, the superconducting magnet 2 is demagnetized.

In step S305, the magnetic pieces 9 are stored in the shim pockets P of the shim trays 1 according to the result obtained through the optimization computation. In step S306, the super conducting magnet 2 is excited, and a static magnetic field is generated again in the FOV 6. In step S307, the magnetic field measurement device measures magnetic field intensity in the FOV 6. In step S308, optimization computation is performed by using the magnetic field intensity measured in step S307, and a magnetic piece amount (B) of the magnetic pieces 9 to be stored in shim pockets P of the shim trays 1 for canceling out the non-homogeneity of the magnetic field is determined.

Here, as the magnetic pieces 9 of the present embodiment, two kinds such as A and B in which thicknesses of square iron sheets are different from each other (for example, B is an iron sheet thinner than A) are prepared, and the kind and the number of magnetic pieces accommodated in a single shim pocket 8 are changed, and thus adjustment to a magnetic piece amount obtained through optimization computation is realized. However, the invention is not limited thereto, and, needless to say, a size and a thickness may be selected as necessary.

In FIG. 6, a shim iron use amount indicates a magnetic piece amount, the unit thereof is a volume [cm³], but this is only an example, in the illustrated example, the shim iron A is a square iron sheet with the size of 20 mm×20 mm and the thickness of 0.1 mm, and the shim iron B is a square iron sheet with the size of 20 mm×20 mm and the thickness of 0.02 mm. Needless to say, these specific values may be arbitrarily set. In the arrangement diagram, numerical values of A and B written for the respective shim pockets indicate the number of magnetic pieces.

In step S309, in a case where the magnetic piece amount (B) is sufficiently smaller than the magnetic piece amount (A) (for example, ¹⁄₁₀ or less), the flow proceeds to step S312, and fine adjustment shimming is performed. If otherwise, the flow proceeds to step S310, the superconducting magnet 2 is demagnetized, and, in step S311, the magnetic pieces 9 of the magnetic piece amount (B) obtained through the optimization computation in step S308 are stored in the shim pockets 8. The flow returns to step S306, and the processes are repeatedly performed.

Steps following step S312 correspond to fine adjustment shimming as a feature of the invention.

In other words, in step S312, the shim tray 1 in which the magnetic pieces 9 are to be disposed is selected as will be described later, and arrangement generating high homogeneity is obtained from selected position arrangements through shimming computation, and a magnetic piece amount (B-2) is determined. An arrangement diagram of the determined magnetic pieces 9 is output and displayed. FIG. 7 illustrates an example of the arrangement diagram. In FIG. 7, shaded regions of the shim pockets (P-1) to (P-5) and (P-20) to (P-24) are selected as restriction regions where the magnetic pieces 9 are not disposed. In other words, a polarity of a magnetic field distribution generated in the FOV 6 by magnetic moment of the magnetic pieces 9 disposed in these regions is positive (refer to FIG. 4), and thus the regions are regions on which the restriction is put as the shim pockets in which the magnetic pieces 9 are not disposed.

Next, in step S313, the magnetic pieces 9 corresponding to the computation result (B-2) are disposed in the shim pockets P of some of the shim trays 1 (for example, shim trays of even numbers #). In step S314, the magnetic field measurement device measures magnetic field intensity in the FOV 6. If the magnetic field intensity measured in step S314 satisfies a desired value of the magnetic field homogeneity in the FOV 6, the shimming is finished. If otherwise, the flow returns to step S312, and the fine adjustment shimming is repeatedly performed.

As in the present embodiment, preferably, the shim trays 1 used for rough adjustment shimming are restricted to shim trays of odd numbers #, and the shim trays 1 used for fine adjustment shimming are restricted to shim trays of even numbers #. Consequently, it is possible to increase the degree of freedom of adjustment of a magnetic piece amount of each shim pocket 8 in fine adjustment shimming.

Figure 8:
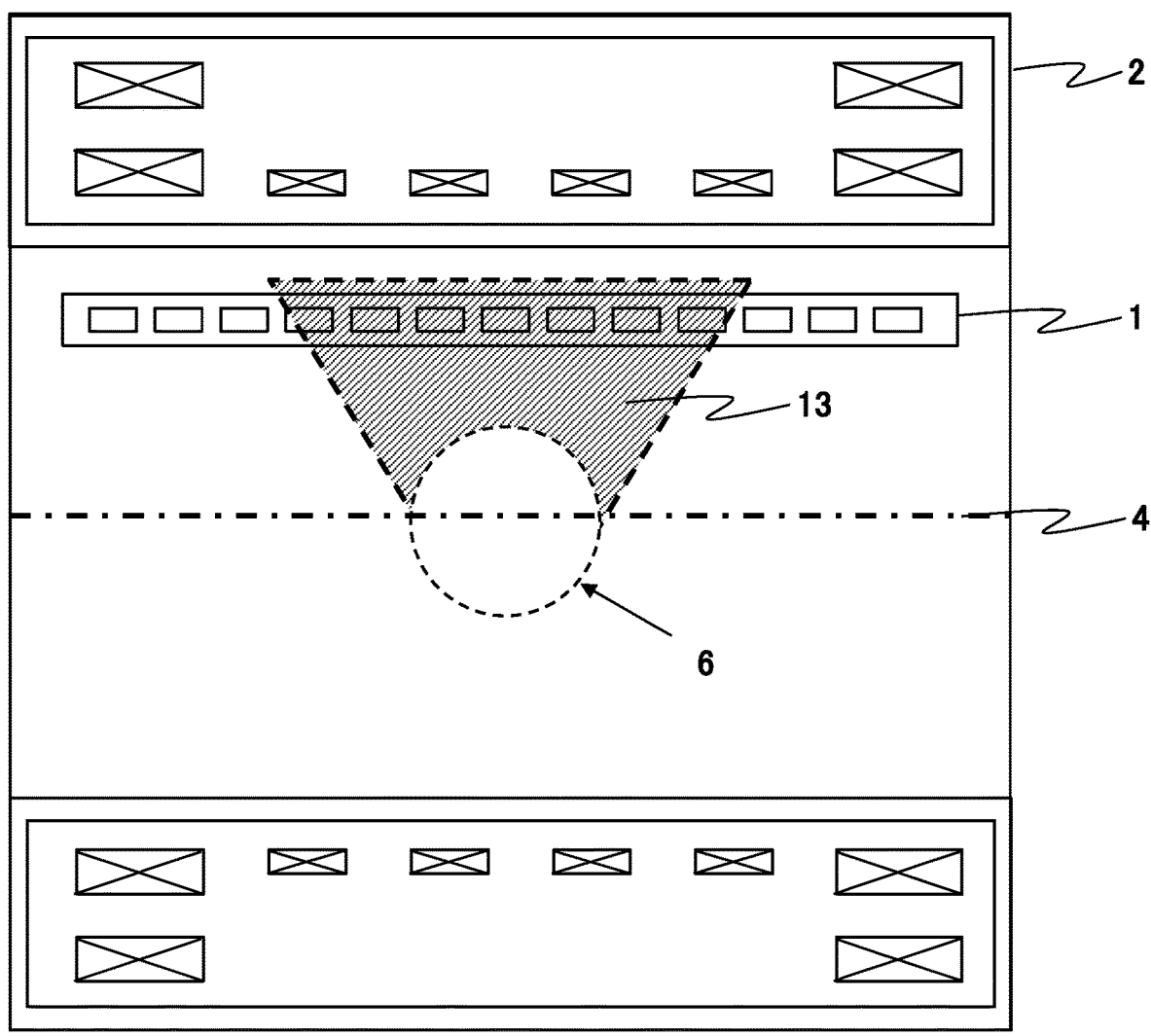
FIG. 8 is a diagram illustrating an adjustment region in fine adjustment shimming according to the first embodiment.

Here, a description will be made of an operation and an effect of the present embodiment with reference to FIGS. 8 and 9. FIG. 8 is a sectional view obtained by cutting the superconducting magnet 2 on a plane passing along the axial direction (Z axis) 4. As illustrated in FIG. 8, out of positive and negative magnetic field distributions generated in the FOV 6 by the magnetic moment of the magnetic piece 9, a region (negative region 11) in which only the negative magnetic field distribution is generated is selected as a region in which the magnetic pieces 9 are disposed. In other words, as illustrated in FIG. 8, in fine adjustment shimming, a range of positions on the shim tray 1 of the magnetic pieces 9 generating the negative magnetic field distribution in the FOV 6 is set as an adjustment region 13, only the shim pockets 8 in the adjustment region 13 are selected, and the magnetic pieces 9 for fine adjustment shimming are disposed therein. In other words, as described above, only the shim pockets (P-6) to (P-19) are selected.

Figure 9:
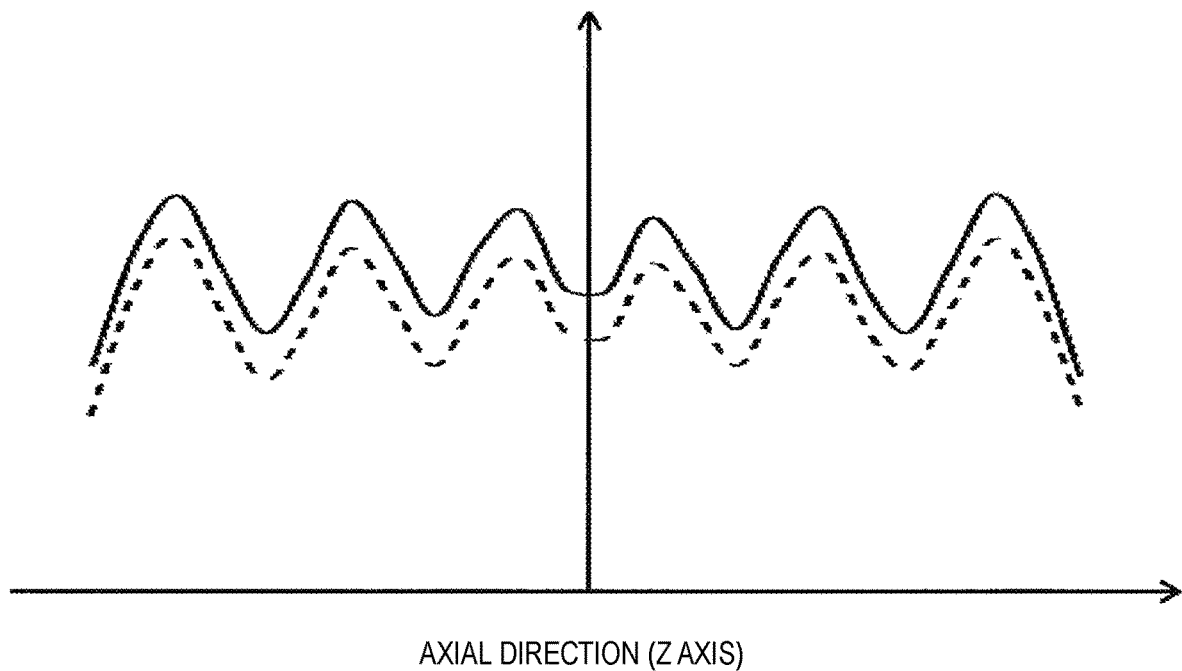
FIG. 9 is a diagram illustrating magnetic field intensity on an FOV surface before and after fine adjustment shimming according to the first embodiment.

According to fine adjustment, shimming of the present embodiment, as illustrated in FIG. 9, it is possible to generate a static magnetic field with high homogeneity. In other words, FIG. 9 illustrates magnetic field intensities on a surface of the FOV 6 before and after the fine adjustment shimming in a comparison manner, in which a longitudinal axis expresses static magnetic field intensity, and a transverse axis expresses an axial direction (Z axis). A solid line indicates a magnetic field intensity before the fine adjustment shimming is performed, and a dashed line indicates magnetic field intensity after the fine adjustment shimming is performed. As can be seen from the figure, there is the selection of arrangement of the magnetic pieces 9 generating a negative magnetic field distribution in the region of the FOV 6 in fine adjustment shimming, and thus magnetic field intensity of the FOV 6 is adjusted to be lowered, and also the magnetic field homogeneity is improved. The magnetic field homogeneity becomes higher as a difference between the maximum value and the minimum value of the solid line or the dashed line becomes smaller. According to the present embodiment, a total use amount of the magnetic pieces 9 can be reduced to about 65% compared with the related art.

In the present embodiment, there is provided a static magnetic field homogeneity adjustment method in an imaging space for a magnetic resonance imaging apparatus, of computing positions of a plurality of magnetic pieces separated from the FOV 6 through shimming computation with respect to a static magnetic field in the FOV (imaging space) 6 generated by a magnetic field generation device of the superconducting magnet 2, and disposing the plurality of magnetic pieces at the positions obtained through the shimming computation, the method including an adjustment step of imposing restriction that a polarity of a magnetic field distribution generated in the FOV 6 by the magnetic pieces disposed at the positions is either positive or negative during the shimming computation, and adjusting the static magnetic field homogeneity.

In the present embodiment, there may be use of a program for computing positions of a plurality of magnetic pieces separated from an imaging space through shimming computation with respect to a static magnetic field in the imaging space generated by a magnetic field generation device, and adjusting static magnetic field homogeneity in the imaging space, the program having a function of imposing restriction that a polarity of a magnetic field distribution generated in the imaging space by the magnetic pieces disposed at the positions is either positive or negative during the shimming computation.

In the present embodiment, there may be use of a computer which computes positions of a plurality of magnetic pieces separated from an imaging space through shimming computation with respect to a static magnetic field in the imaging space generated by a magnetic field generation device, and adjusts static magnetic field homogeneity in the imaging space, the computer having a function of imposing restriction that a polarity of a magnetic field distribution generated in the imaging space by the magnetic pieces disposed at the positions is either positive or negative during the shimming computation.

The direction 12 of magnetic moment of the magnetic piece 9 may be parallel to a direction of a static magnetic field of the FOV 6. In this case, a position of the magnetic piece 9 where the magnetic piece 9 generates a negative magnetic field distribution in the FOV 6 is selected.

A boundary of a selected position of the magnetic piece 9 is a boundary at which a negative magnetic field distribution generated in the FOV 6 by the magnetic piece 9 satisfies Equation 4. The negative region 11 may be obtained by solving Equation 4. In addition, in fine adjustment shimming, each shim pocket 8 from a bore opening of the superconducting magnet 2 is selected so that the magnetic piece 9 is not disposed therein, and the negative region 11 may be estimated by evaluating magnetic field homogeneity predicted after the shimming is completed, and a change in a magnetic piece amount (B-2) used for the shimming.

Figure 10:
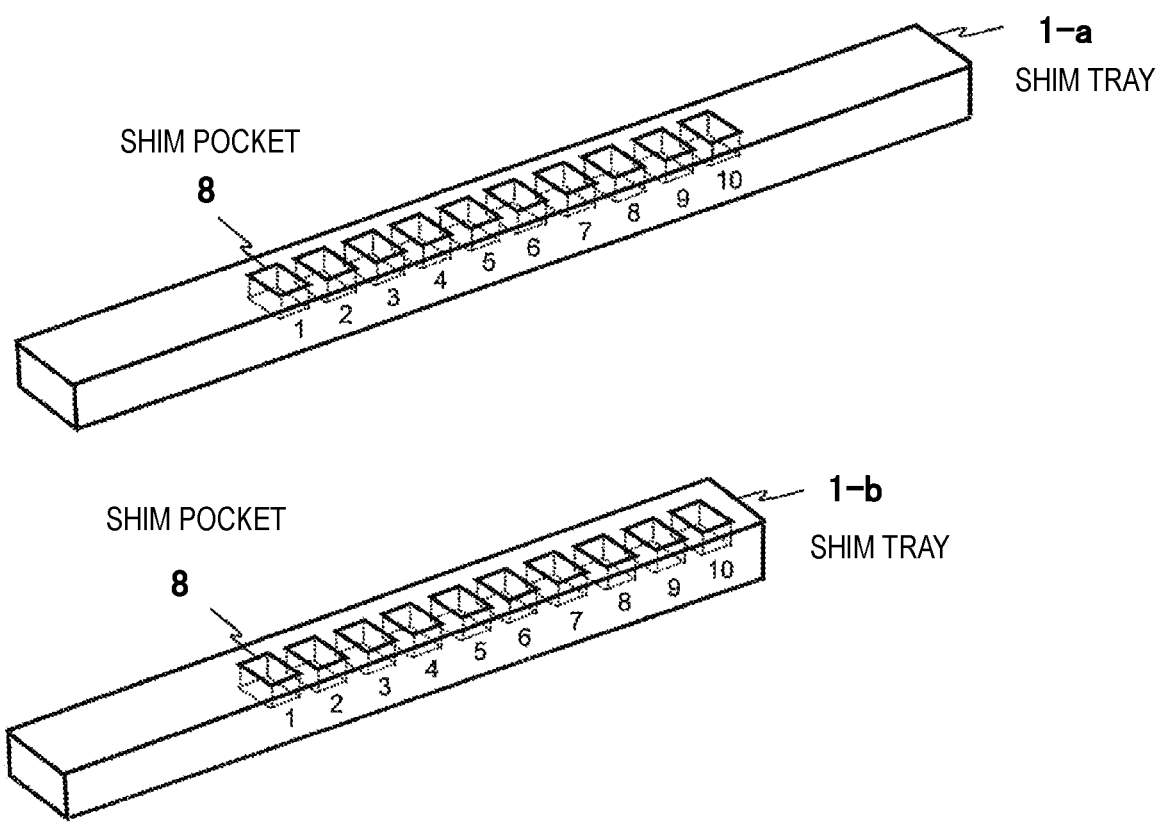
FIG. 10 is a diagram illustrating a modification example of a shim tray used for fine adjustment shimming according to the first embodiment.

The shim pockets 8 used for fine adjustment shimming of the present embodiment are shim pockets in a region close to the FOV 6. For example, the region is a region corresponding to about 35% of the entire length of the shim tray 1 on one side from a central position of the FOV 6. Therefore, the shim tray 1 used for fine adjustment shimming of the present embodiment may be predefined so as to be formed as illustrated in FIG. 10. As in a shim tray 1-a illustrated in FIG. 10(a), the shim pockets 8 may be disposed in a region of about 80% of the entire length of the shim tray 1 with the center of the FOV 6 as a reference. As in a shim tray 1-B, the shim tray may be shortened by cutting either one of ends of the shim tray 1-a in the axial direction.

The magnetic resonance imaging apparatus of the present embodiment includes the superconducting magnet 2 which is a magnetic field generation device in which an FOV (imaging space) is formed in a cylindrical inner space by a cylindrical electromagnet, a plurality of shim trays 1 which are linear magnetic body holding members holding the magnetic pieces 9 are disposed on an inner circumferential surface of the electromagnet in a distribution manner, and the shim pockets 8 which are a plurality of depressions for accommodation of the magnetic pieces 9 are arranged in a longitudinal direction of the shim tray 1. Therefore, in a case of using the shim trays in FIG. 10, it is necessary to properly use the shim trays for rough adjustment shimming and fine adjustment shimming. In this case, for example, shim adjustment is performed by using shim trays of odd numbers # for rough adjustment, and by using shim trays of even numbers # for fine adjustment.

In this case, in the magnetic resonance imaging apparatus including the magnetic field generation device which forms the imaging space in the cylindrical inner space by using the cylindrical electromagnet, and a plurality of linear magnetic body holding members which are disposed on the inner circumferential surface of the electromagnet along the axial direction and hold magnetic pieces for magnetic field adjustment and in which a plurality of depressions for accommodation of the magnetic pieces are arranged in the longitudinal direction of the magnetic body holding member, the magnetic resonance imaging apparatus includes some of the plurality of magnetic body holding members in which the depressions for accommodation of the magnetic pieces are not arranged over a set length from an end of each of the magnetic body holding members.

In the description of the present embodiment, as illustrated in FIG. 8, the description has been made of a case where a range of positions on the shim tray 1 of the magnetic pieces 9 generating a negative magnetic field distribution in the FOV 6 is referred to as the adjustment region 13, and the magnetic pieces 9 for fine adjustment shimming are disposed in the shim pockets 8 in the adjustment region 13. However, the invention is not limited thereto. The magnetic pieces 9 may be disposed in the shim pockets 8 of the negative region 11 deviated from the adjustment region 13. In this case, weights of the magnetic pieces 9 to be disposed in the negative region 11 deviated from the adjustment region 13, and the adjustment region 13 are replaced with each other. For example, a small amount of the magnetic pieces 9 are disposed in the negative region 11 deviated from the adjustment region 13.

Second Embodiment

Figure 11:
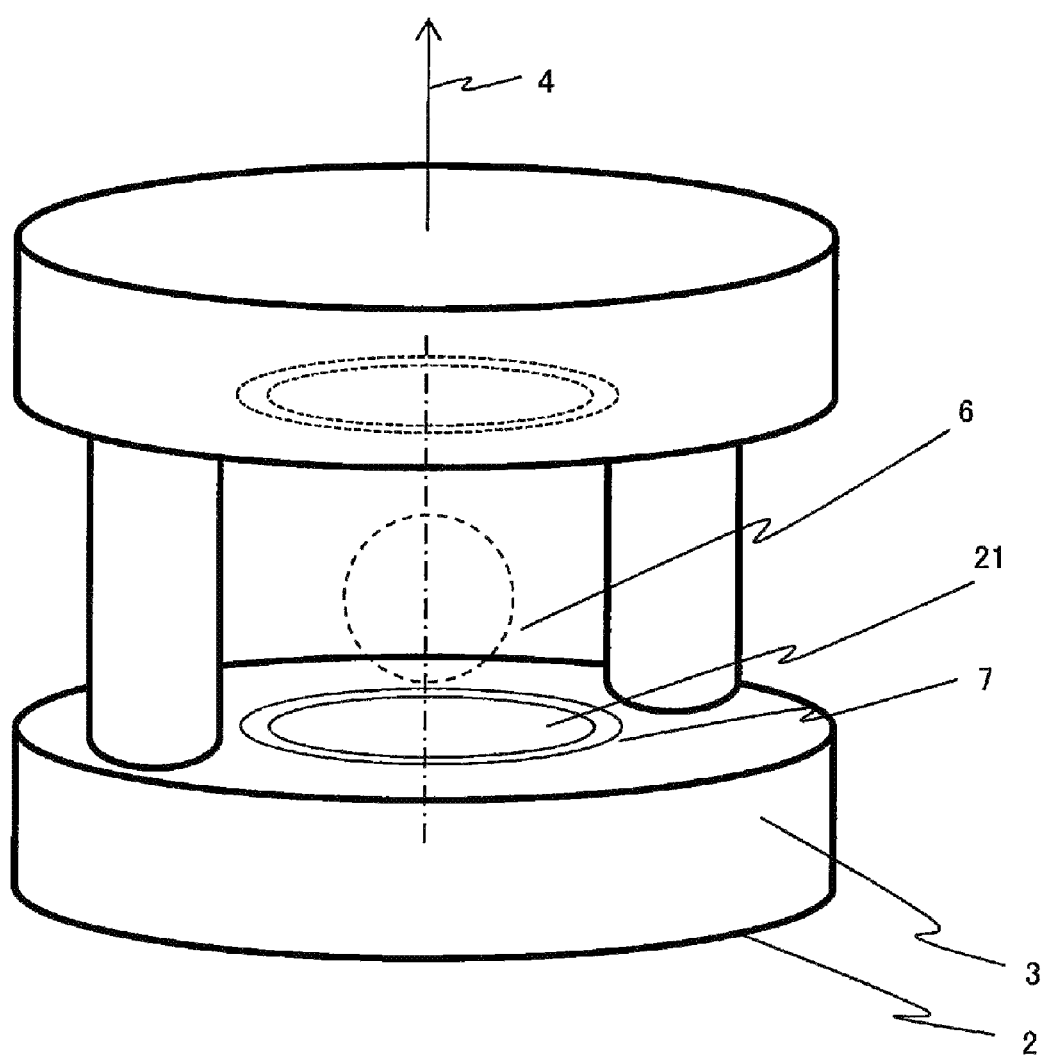
FIG. 11 is a schematic configuration diagram of an open type superconducting magnet including a shimming mechanism of a magnetic resonance imaging apparatus according to a second embodiment of the invention.

FIG. 11 is a schematic exterior perspective view of an open type superconducting magnet 2 of a magnetic resonance imaging apparatus according to a second embodiment. A difference from the first embodiment is that the open type superconducting magnet 2 is applied to fine adjustment shimming of the invention instead of the cylindrical superconducting magnet. In a case of the open type superconducting magnet 2, an orientation of a generated magnetic field of the FOV 6 is a vertical direction. Hereinafter, only the difference will be described, and the same content will not be described. A description will be made of a static magnetic field homogeneity adjustment method for the open type superconducting magnet 2 with reference to FIGS. 12 to 17.

As illustrated in FIG. 11, the superconducting magnet 2 in which a magnetic field is open is formed by accommodating superconducting coils in a pair of vacuum containers 3 which are vertically located on upper and lower sides. The open type superconducting magnet 2 forms an FOV 6 with an axial direction (Z axis) 4 which is parallel to a vertical direction as a central axis. A pair of disc-shaped shim trays 21 with the Z axis 4 as a central axis are provided on facing upper and lower surfaces of the superconducting magnet 3. Although not illustrated, a plurality of rectangular hole-like shim pockets 22 are provided at an equal interval in a lattice form on a surface of each of the pair of shim trays 21 on the FOV 6 side.

Figure 12:
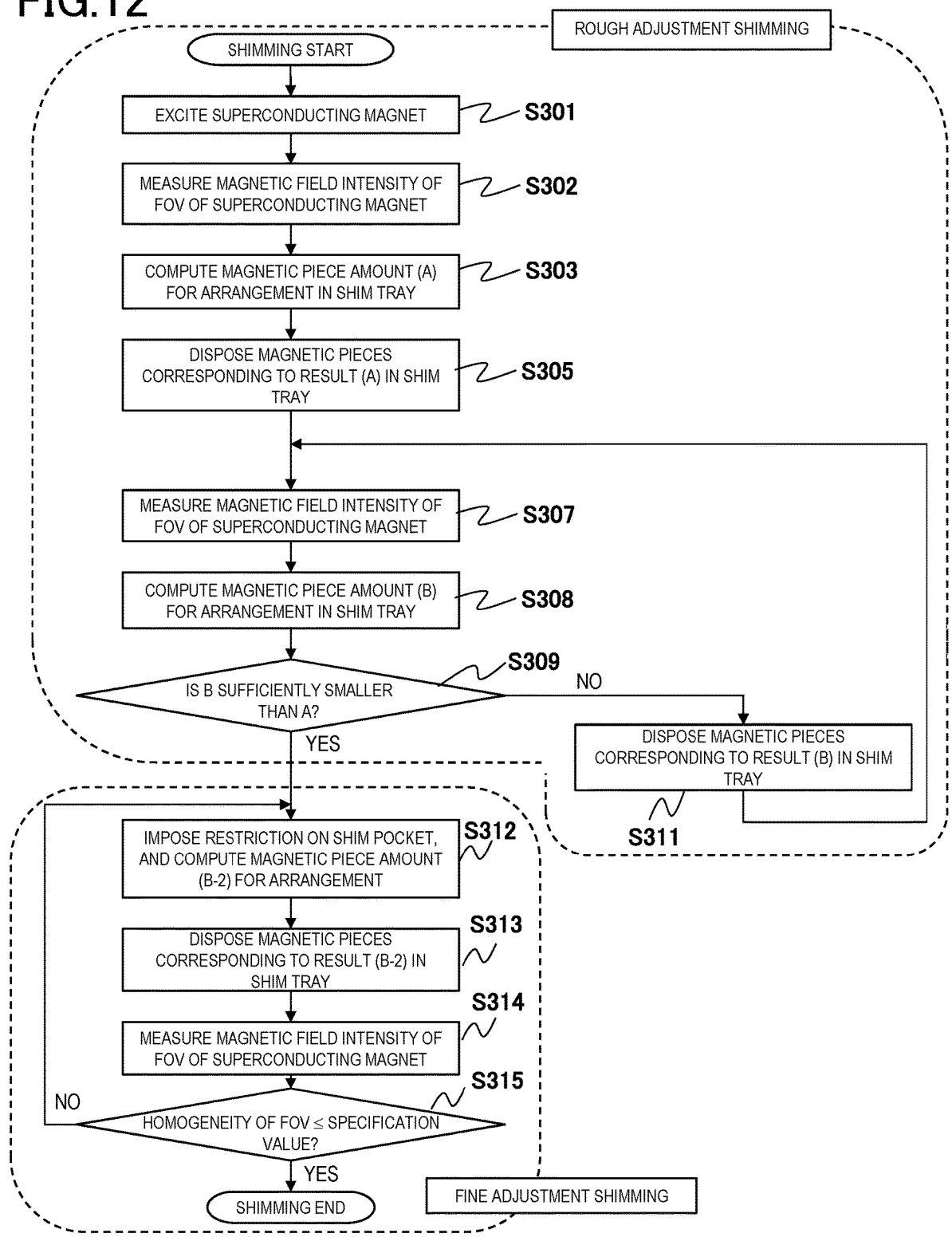
FIG. 12 is a flowchart illustrating shimming according to the second embodiment.

FIG. 12 is a flowchart illustrating shimming process procedures according to the static magnetic field adjustment method of the present embodiment. Since the open type superconducting magnet 2 is excited only once, and continuously performs shimming without being demagnetized, the processes in steps S304, S306 and S310 of FIG. 3 in the first embodiment may be omitted. In other words, this is because, in a case of the cylindrical superconducting magnet 2, strong magnetic force of the superconducting magnet 2 acts on the shim trays 21, the shim trays 21 cannot be extracted in order to accommodate the magnetic pieces 9 unless demagnetization is performed. In contrast, in a case of the open type superconducting magnet 2, magnetic force acting on the individual magnetic piece 9 accommodated in the shim pocket 8 is relatively weak, and thus an operation of accommodating the magnetic piece 9 is not hindered even if demagnetization is not performed.

FIGS. 13 and 14 are arrangement diagrams of the magnetic pieces 9 used for shimming according to the second embodiment. As illustrated, the disc-shaped shim tray 21 has shim tray numbers (#1 to #12) in a plurality of rows, and is formed to have a plurality of shim pockets 22 at lattice positions where the shim tray lumbers (#1 to #12) correspond to shim pocket numbers (A to L). Each shim pocket 22 is formed in a rectangular hole which can accommodate the magnetic pieces 9 in the same manner as in the first embodiment. In fine adjustment shimming, as illustrated in FIG. 14, among positive and negative magnetic field distributions generated in the FOV 6 by magnetic moment, of the magnetic pieces 9, only the shim pockets 22 in a region, in which the positive region 10 is generated are used. In other words, the shaded shim pockets 22 correspond to the negative region 11, and thus are not used.

Figure 15:
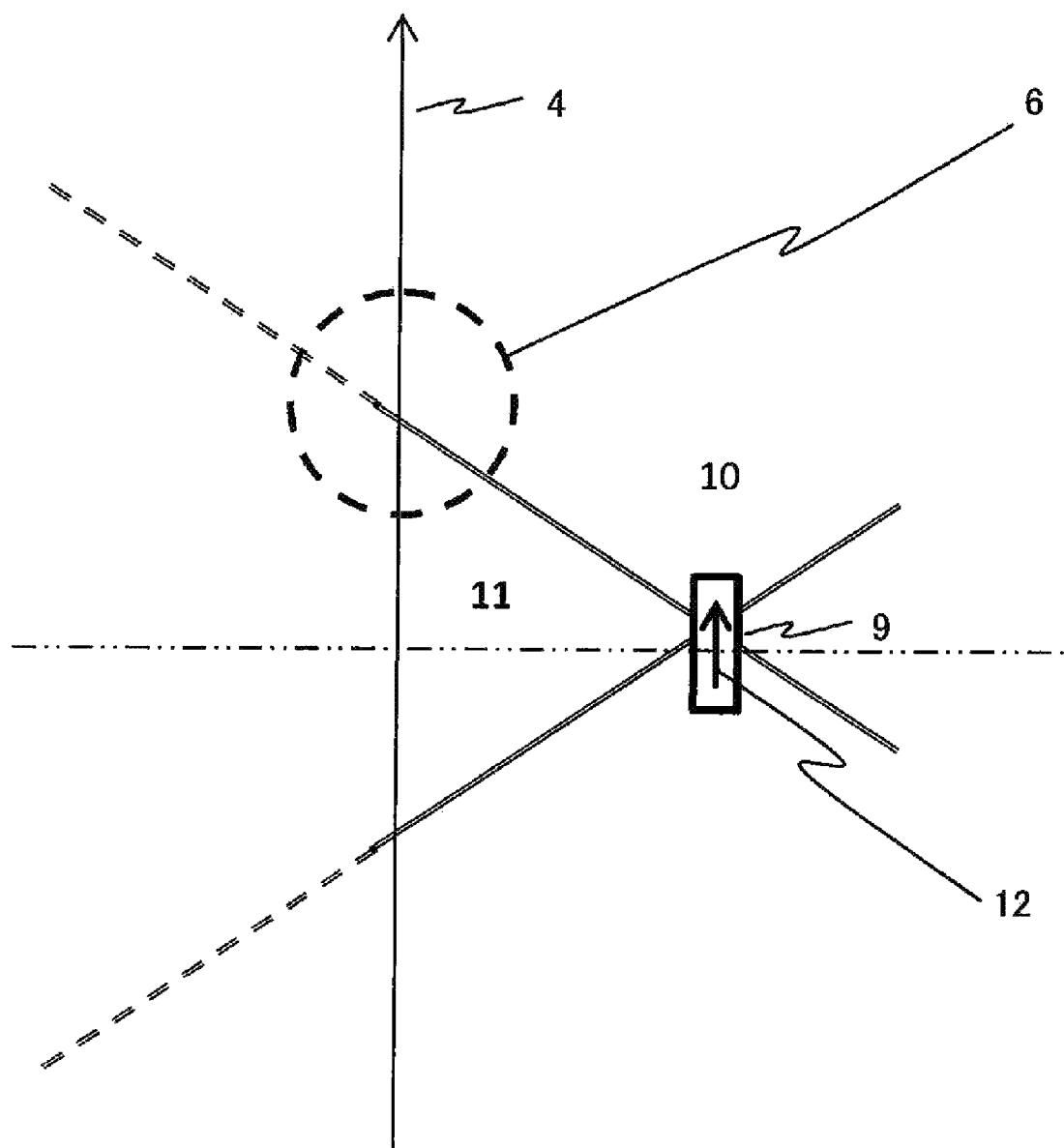
FIG. 15 is a diagram illustrating positive and negative magnetic field distributions generated in an FOV by magnetic moment of magnetic pieces according to the second embodiment.

FIG. 15 is a diagram illustrating positive and negative magnetic field distributions generated in the FOV 6 by magnetic moment of the magnetic pieces 9 according to the present embodiment. The superconducting magnet 2 mainly generates a vertically upward magnetic field in the region of the FOV 6. However, needless to say, fine adjustment shimming of the invention is also applicable to a case where a vertically downward magnetic field is mainly generated in the FOV 6.

Figure 16:
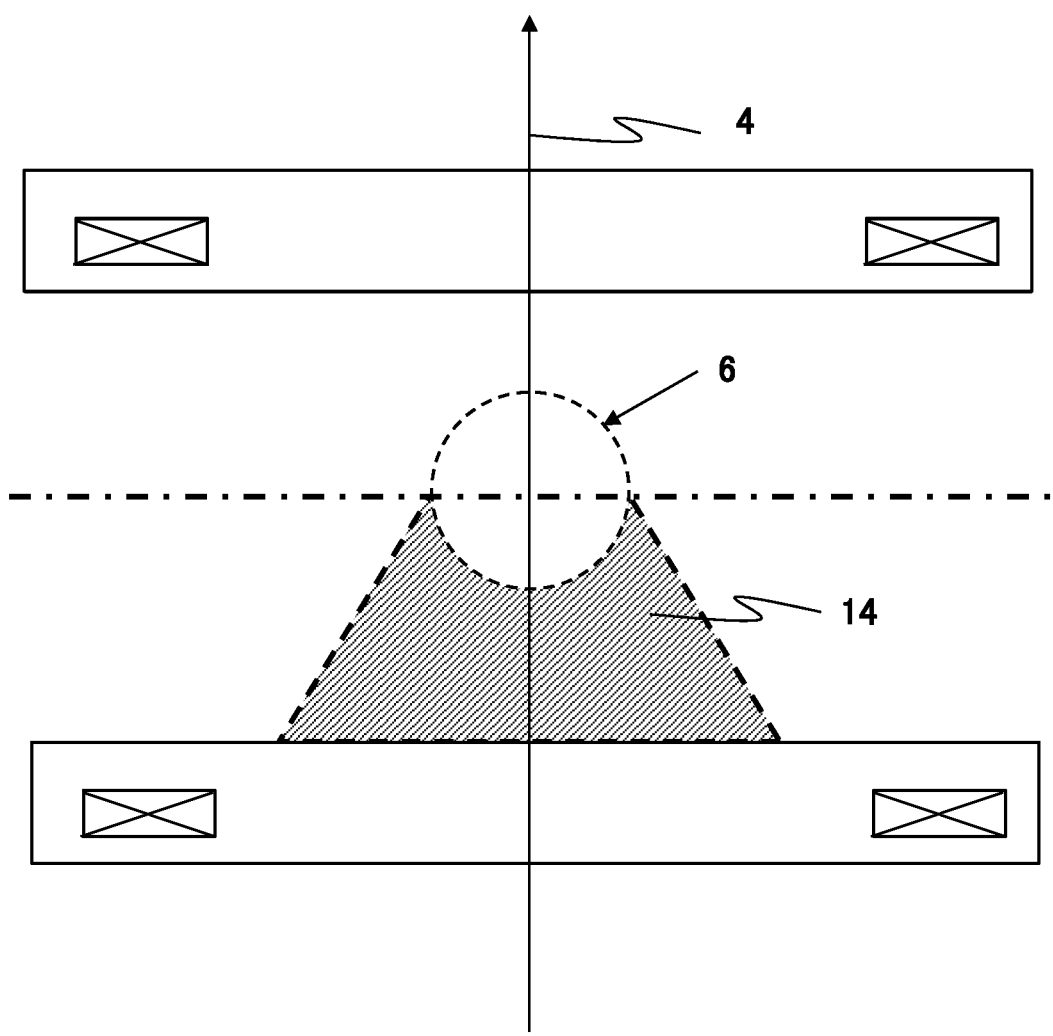
FIG. 16 is a diagram illustrating an adjustment region in fine adjustment shimming according to the second embodiment.

FIG. 16 illustrates an adjustment region 13 in fine adjustment shimming. In the fine adjustment shimming, a region of the shim pockets 22 in which a positive magnetic field is generated in the FOV 6 by magnetic moment of the magnetic pieces 9 is selected, and a region for arrangement of the magnetic pieces 9 is selected as an arrangement region 14.

Figure 17:
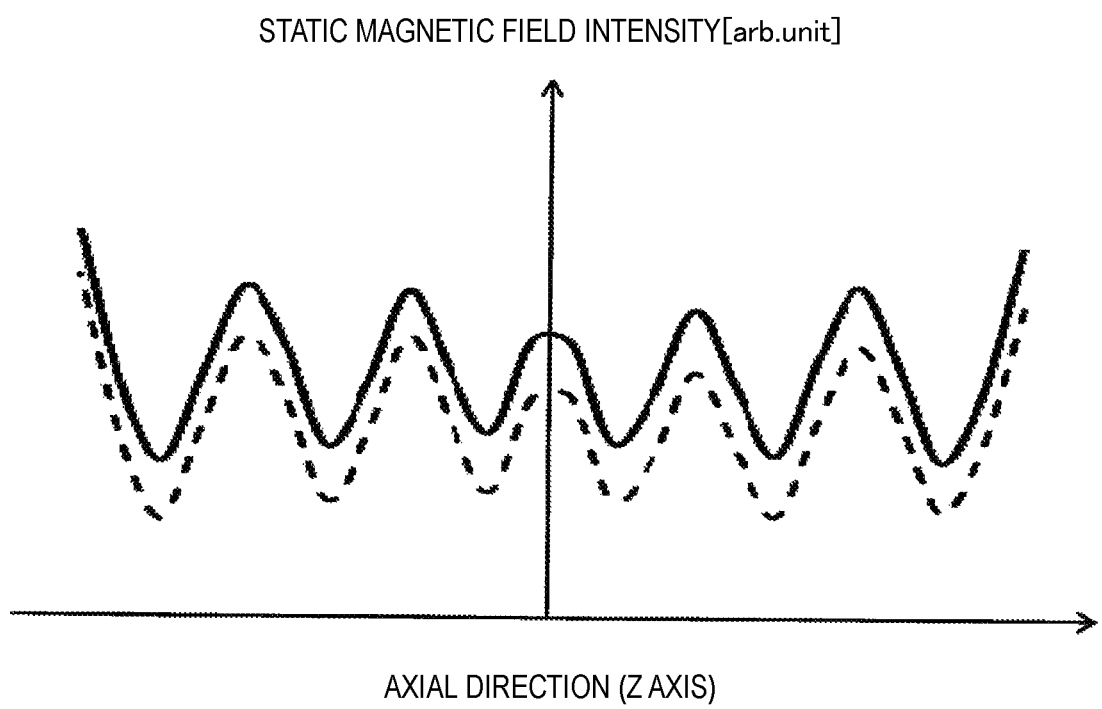
FIG. 17 is a diagram illustrating magnetic field intensity on an FOV surface before and after fine adjustment shimming according to the second embodiment.

FIG. 17 illustrates magnetic field intensities on a surface of the FOV 6 before and after the fine adjustment shimming. In a case where a longitudinal axis expresses static magnetic field intensity, and a transverse axis expresses an axial direction (Z axis) 4, a solid line indicates a magnetic field intensity before the fine adjustment shimming is performed, and a dashed line indicates magnetic field intensity after the fine adjustment shimming is performed. In the fine adjustment shimming of the present embodiment, since the homogeneity is adjusted by using the magnetic pieces 9 generating a magnetic field distribution in the positive region 10 of the region of the FOV 6, magnetic field intensity changes to increase, and the homogeneity is adjusted.

The second embodiment corresponds to a case where a direction 12 of magnetic moment of the magnetic piece 9 is orthogonal to a direction of a static magnetic field of the FOV 6. In this case, there is a feature that a position of the magnetic piece 9 where the magnetic piece 9 generates a positive magnetic field distribution in the FOV 6 is selected.

In the second embodiment, a description has been made of an example in which, as illustrated in FIG. 16, the region of the shim pockets 22 in which magnetic moment of the magnetic piece 9 generates a positive magnetic field in the FOV 6 is selected, in other words, the magnetic piece 9 for fine adjustment shimming is disposed in the adjustment region 14 in which the positive region 10 overlaps the region of the FOV 6. However, the invention is not limited thereto. The magnetic pieces 9 may be disposed in the positive region 10 deviated from the adjustment region 14. In this case, weights of the magnetic pieces 9 to be disposed in the positive region 10 deviated from the adjustment region 14, and the shim pockets 22 of the adjustment region 14 are replaced with each other. For example, a small amount of the magnetic pieces 9 are disposed in the positive region 10 deviated from the adjustment region 14.

The magnetic resonance imaging apparatus to which the static magnetic field homogeneity adjustment method of the first embodiment or the second embodiment is applied includes a magnetic field generation device that is provided with an electromagnet forming a static magnetic field in an imaging space; and magnetic body holding members in which a plurality of depressions for accommodation of magnetic pieces for magnetic field adjustment are arranged on a surface portion of the electromagnet on the imaging space side, in which the density of an amount of magnetic pieces accommodated in a portion of each of the magnetic body holding members close to the imaging space is higher than the density of an amount of magnetic pieces in a portion thereof distant from the imaging space.

As mentioned above, the invention has been described on the basis of the embodiments, but the invention is not limited to these embodiments, it is obvious to a person skilled in the art that the invention may be embodied in modified or changed forms within the scope of the invention, and the modified or changed forms are naturally included in the claims of the present application.

REFERENCE SIGNS LIST 1, 1-B, and 21 Shim Tray, 2 Superconducting Magnet, 3 Vacuum Container, 4 Axial Direction (Z Axis), 5 Cylindrical Bore, 6 FOV, 7 Gradient Magnetic Field Coil, 8 and 22 Shim Pocket, 9 Magnetic Piece, 10 Positive Region, 11 Negative Region, 12 Orientation of Magnetization of Magnetic Piece, 13 Adjustment Region, 14 Adjustment Region

The invention claimed is:

1. A static magnetic field homogeneity adjustment method for a magnetic resonance imaging apparatus in an imaging space of computing positions of a plurality of magnetic pieces separated from the imaging space through shimming computation with respect to a static magnetic field in the imaging space generated by a magnetic field generation device, and disposing the plurality of magnetic pieces at the positions obtained through the shimming computation, the method comprising:

an adjustment step of imposing restriction that a polarity of a magnetic field distribution generated in the imaging space by the magnetic pieces disposed at the positions is either positive or negative during the shimming computation, and adjusting the static magnetic field homogeneity, wherein, in a case where a direction of magnetic moment of the magnetic pieces is parallel to a direction of the static magnetic field, positions of the magnetic pieces where the magnetic pieces generate a negative magnetic field distribution in the imaging space are selected.

2. A static magnetic field homogeneity adjustment method for a magnetic resonance imaging apparatus in an imaging space of computing positions of a plurality of magnetic pieces separated from the imaging space through shimming computation with respect to a static magnetic field in the imaging space generated by a magnetic field generation device, and disposing the plurality of magnetic pieces at the positions obtained through the shimming computation, the method comprising:

an adjustment step of imposing restriction that a polarity of a magnetic field distribution generated in the imaging space by the magnetic pieces disposed at the positions is either positive or negative during the shimming computation, and adjusting the static magnetic field homogeneity, wherein, in a case where a direction of magnetic moment of the magnetic pieces is orthogonal to a direction of the static magnetic field, positions of the magnetic pieces where the magnetic pieces generate a positive magnetic field distribution in the imaging space are selected.

3. The static magnetic field homogeneity adjustment method for a magnetic resonance imaging apparatus according to claim 1, wherein a boundary of selected positions of the magnetic pieces is a boundary at which positive and negative magnetic field distributions generated in the imaging space by the magnetic pieces satisfy the following equation:

$$\frac{3M_z \cdot Z^2}{r^5} - \frac{M_z}{r^3} =.$$

where Z is a position in a static magnetic field direction (Z axis direction), r is a distance from magnetic moment, and Mz is magnetic moment [$Am^2$] in the static magnetic field direction (Z axis direction).

4. A static magnetic field homogeneity adjustment method for a magnetic resonance imaging apparatus in an imaging space of computing positions of a plurality of magnetic pieces separated from the imaging space through shimming computation with respect to a static magnetic field in the imaging space generated by a magnetic field generation device, and disposing the plurality of magnetic pieces at the positions obtained through the shimming computation, the method comprising:

an adjustment step of imposing restriction that a polarity of a magnetic field distribution generated in the imaging space by the magnetic pieces disposed at the positions is either positive or negative during the shimming computation, and adjusting the static magnetic field homogeneity, wherein, in the adjustment step of disposing the magnetic pieces, each location from a bore opening of the magnetic field generation device is selected so that a magnetic piece is not disposed therein, and a negative region is estimated by evaluating magnetic field homogeneity predicted after the adjustment step is completed, and a magnetic piece amount used for the adjustment step is changed.

5. A magnetic resonance imaging apparatus comprising:
   a magnetic field generation device that is provided with an electromagnet forming a static magnetic field in an imaging space; and
   magnetic body holding members in which a plurality of depressions for accommodation of magnetic pieces for magnetic field adjustment are arranged on a surface portion of the electromagnet on the imaging space side,
   wherein the density of an amount of magnetic pieces accommodated in a portion of each of the magnetic body holding members close to the imaging space is higher than the density of an amount of magnetic pieces in a portion thereof distant from the imaging space,
   wherein the magnetic field generation device includes a cylindrical electromagnet forming the imaging space in a cylindrical inner space,
   wherein the magnetic body holding members are distributed on an inner circumferential surface of the electromagnet, and each of the magnetic body holding members is provided with a plurality of depressions which are disposed in an axial direction and accommodate the magnetic pieces in a longitudinal direction, and
   wherein the depressions are not formed over a set length from both ends in some of the magnetic body holding members.

6. The magnetic resonance imaging apparatus according to claim 5,
   wherein, in some of the magnetic body holding members, at least a length of one end side where the depressions are not formed is shorter than a length of the other side.

* * * * *